US010489617B2

United States Patent
Salem et al.

(10) Patent No.: US 10,489,617 B2
(45) Date of Patent: Nov. 26, 2019

(54) SYSTEMS AND METHODS FOR INDUCTIVE IDENTIFICATION

(71) Applicant: CareFusion 303, Inc., San Diego, CA (US)

(72) Inventors: Mooneer Thabet Salem, San Diego, CA (US); Lawrence Farhat, Oceanside, CA (US)

(73) Assignee: CAREFUSION 303, INC., San Diego, CA (US)

( * ) Notice: Subject to any disclaimer, the term of this patent is extended or adjusted under 35 U.S.C. 154(b) by 650 days.

(21) Appl. No.: 14/811,667

(22) Filed: Jul. 28, 2015

(65) Prior Publication Data

US 2017/0032152 A1 Feb. 2, 2017

(51) Int. Cl.
*G06K 7/08* (2006.01)
*G06K 19/077* (2006.01)
(Continued)

(52) U.S. Cl.
CPC .............. *G06K 7/086* (2013.01); *A61M 5/142* (2013.01); *F04B 53/16* (2013.01);
(Continued)

(58) Field of Classification Search
CPC .............. G06K 7/10009; G06K 7/086; G06K 19/0672; G06K 19/077; A61M 5/142;
(Continued)

(56) References Cited

U.S. PATENT DOCUMENTS 4,142,674 A * 3/1979 Walton ............... G06K 19/0672
235/442
4,165,033 A * 8/1979 Nielsen ............... A01K 11/006
235/439
(Continued)

FOREIGN PATENT DOCUMENTS

EP          1048006 B1    6/2004
WO     WO-9935610 A1 *  7/1999    ............. G06K 1/125
(Continued)

OTHER PUBLICATIONS

LDC1612, LDC1614 Multi-Channel 28-Bit Inductance to Digital Converter (LDC) for Inductive Sensing, Texas Instruments Incorporated, Dec. 2014, 58 pages, Dallas, Texas.
(Continued)

*Primary Examiner* — Nathan C Zollinger
(74) *Attorney, Agent, or Firm* — Morgan, Lewis & Bockius LLP

(57) ABSTRACT

Inductive identification systems and methods are described. The system may include an inductive detector configured to identify objects having inductive identifiers. An inductive detector may include conductive coils and inductance readout circuitry for measuring an inductance of each coil. An inductive identifier may include a conductive pattern configured to induce a desired inductance in the coils of the inductive detector. An inductive identifier may include a film having openings, each opening configured to be disposed over a corresponding coil to induce differing inductance changes in the corresponding coils. A pattern of inductance
(Continued)

values may be determined and used to identify the object. The detector may be implemented in a cassette recess of an infusion pump system. The inductive identifier may be disposed on a pump cassette configured to be received in the cassette recess and identified based on an inductive interaction between the inductive detector coils and the inductive identifier.

19 Claims, 11 Drawing Sheets

(51) Int. Cl.
 *A61M 5/142* (2006.01)
 *F04B 53/16* (2006.01)
 *G06K 7/10* (2006.01)
 *G06K 19/067* (2006.01)
 *F04B 43/02* (2006.01)
(52) U.S. Cl.
 CPC ..... *G06K 7/10009* (2013.01); *G06K 19/0672* (2013.01); *G06K 19/077* (2013.01); *A61M 2005/14208* (2013.01); *A61M 2205/60* (2013.01); *F04B 43/02* (2013.01)
(58) Field of Classification Search
 CPC ..... A61M 2005/14208; A61M 2205/60; F04B 43/02; F04B 49/22; F04B 53/10; F04B 53/16
 See application file for complete search history.

(56) References Cited

U.S. PATENT DOCUMENTS

| | | | |
|---|---|---|---|
| 4,878,896 A * | 11/1989 | Garrison | A61M 5/142 604/65 |
| 5,278,555 A | 1/1994 | Hoekman | |
| 5,531,697 A * | 7/1996 | Olsen | A61M 5/142 604/131 |
| RE37,956 E * | 1/2003 | Blama | G06K 19/0672 235/435 |
| 6,727,691 B2 | 4/2004 | Goldfine et al. | |
| 8,011,905 B2 * | 9/2011 | Artsyukhovich | A61M 1/0058 417/474 |
| 8,394,081 B2 * | 3/2013 | Locke | A61M 1/0058 604/543 |
| 2017/0213012 A1 * | 7/2017 | O'Scolai | G06F 19/3468 |

FOREIGN PATENT DOCUMENTS

| | | | | |
|---|---|---|---|---|
| WO | WO-2008017146 A1 | | 2/2008 | |
| WO | WO 2009126999 A1 * | | 10/2009 | ......... G06K 19/0723 |

OTHER PUBLICATIONS

International Search Report and Written Opinion for Application No. PCT/US2016/041615, dated Oct. 19, 2016, 10 pages.

* cited by examiner

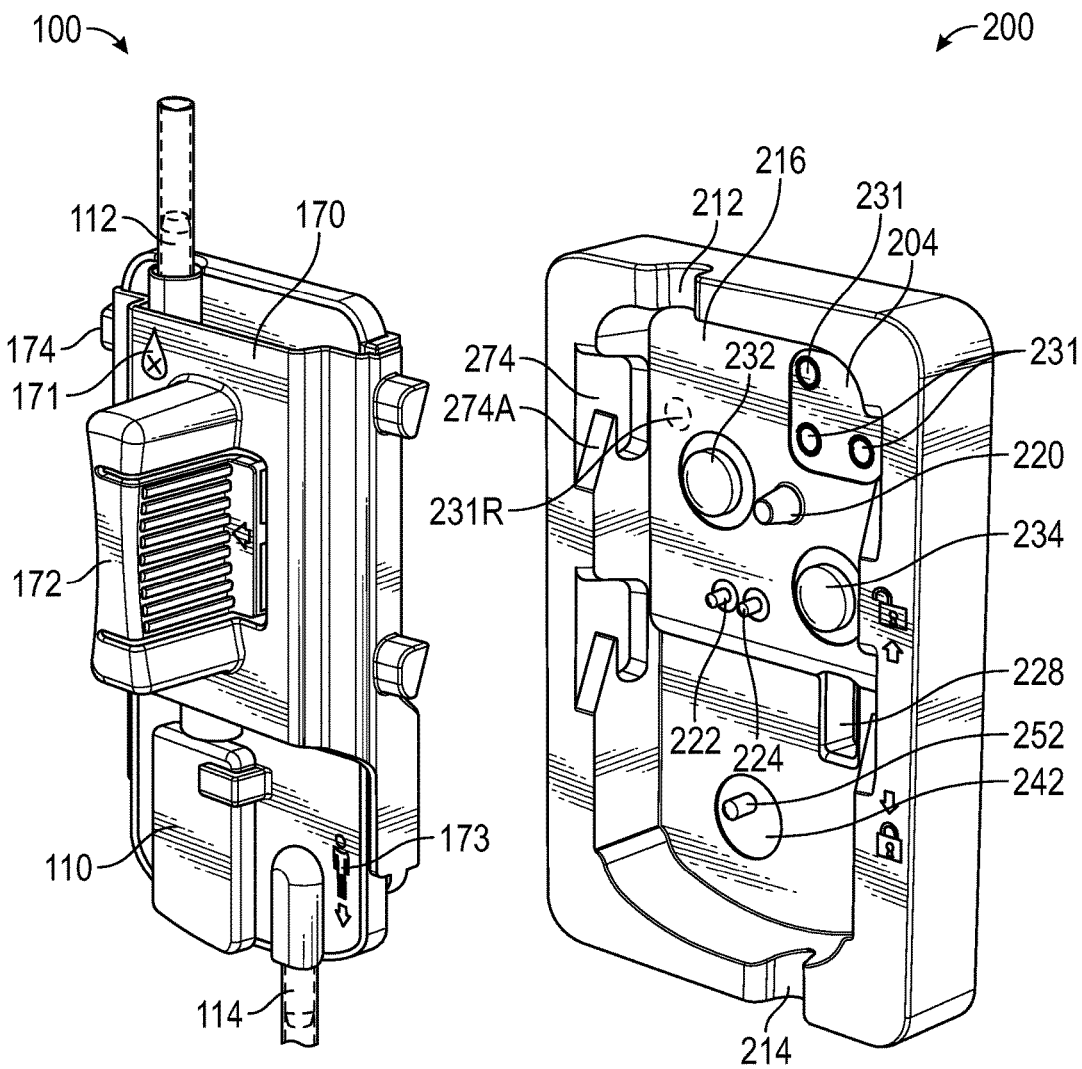

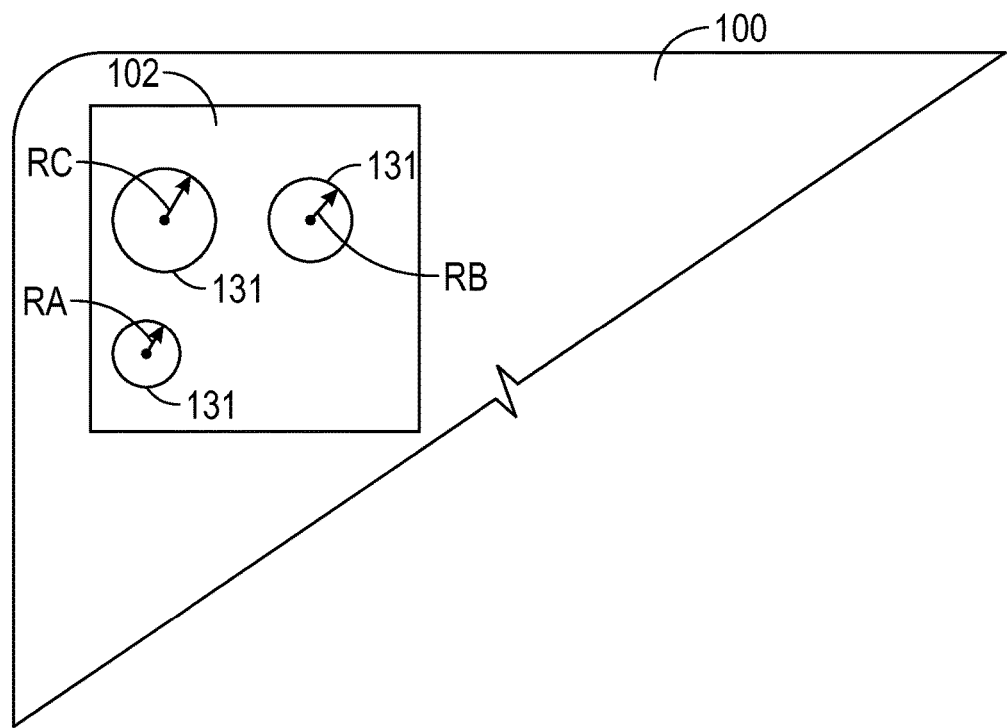
FIG. 7
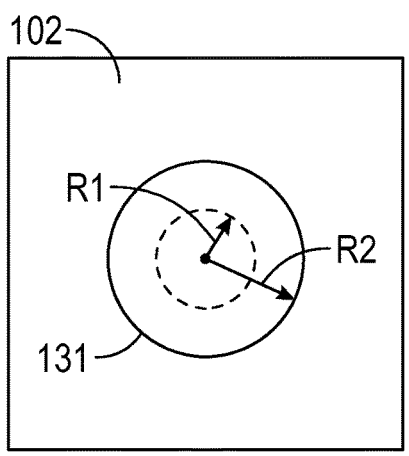 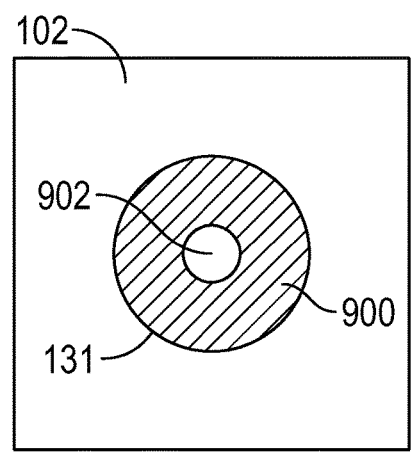
FIG. 8  FIG. 9

SYSTEMS AND METHODS FOR INDUCTIVE IDENTIFICATION

TECHNICAL FIELD

The present disclosure generally relates to apparatus, systems, and methods of identification, and more particularly to inductive identification systems and associated methods.

BACKGROUND

Technological systems for electronic identification of objects are widespread and include optical scanners of bar codes or quick-response codes at retail stores and other locations and radio-frequency identification (RFID) tags that emit radio-frequency signals containing identifying information for objects such as livestock, consumer products, and shipping containers.

In some situations, accurate identification of an object can be critical. For example, infusion pumps are medical devices that may be used to administer intravenous (IV) fluids. An infusion pump can facilitate the delivery of IV fluids while controlling the volumes and rates for the delivery of such IV fluids. A typical infusion pump manipulates an IV tube or IV cartridge such that the IV fluid moves from a container to a patient. The IV tube or IV cartridge is typically connected to or integrated with an IV set (e.g., tubing, valves, filter, check valves, injection ports, and fittings for delivering fluid to a patient), and therefore the cartridge and IV set may be disposable to reduce the risk of infection and contamination. Thus, identification of a particular disposable cartridge and IV set coupled to the pump may be important so that the IV fluids are properly delivered to the patient and medical errors are avoided.

Particularly for disposable objects, it would be desirable to be able to provide identification systems and methods that reduce the cost and complexity of object identification relative to conventional bar code and RFID systems without reducing the accuracy and reliability of the identification.

SUMMARY

Aspects of the subject technology relate to inductive identification of objects. Some aspects of the subject technology relate to identification of disposable IV pump cassettes using infusion pump systems having inductive detectors.

In accordance with certain aspects, an apparatus may include at least one conductive coil; and processing circuitry coupled to the at least one conductive coil and configured to (a) determine an inductance of the at least one conductive coil and (b) determine an identity of an object based on the inductance when an inductive identifier of the object is placed within a proximal distance of the at least one conductive coil.

In accordance with certain aspects, a pump cassette may include a rigid body comprising a compliant membrane that defines a controllable fluid pathway that extends from an inlet port to an outlet port; and an inductive identifier having a coded pattern that identifies the pump cassette.

In accordance with certain aspects, an infusion pump system may include a processing unit; and a cassette recess adapted to receive a pump cassette, the cassette recess including an inductive cassette detector; and a plurality of mechanisms operably coupled to the processing unit and configured to control fluid flow in pump cassette.

It is understood that in accordance with certain aspects, the cassette recess may be integrated into the same box as the processing unit or may be contained in an interface module that may be operatively coupled to the processing unit.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings:

FIGS. 2A and 2B illustrate perspective views of examples of an embodiment of a disposable IV pump cassette and cassette recess, in accordance with aspects of the present disclosure.

FIG. 7 illustrates a diagram of an example embodiment of a pump cassette having an inductive identifier film, in accordance with aspects of the present disclosure.

FIG. 8 illustrates a top view of an example embodiment of an inductive identifier film showing how features of various sizes on the film can be used to encode identifying information, in accordance with aspects of the present disclosure.

FIG. 9 illustrates a top view of an example embodiment of an inductive identifier film having multiple embedded features, in accordance with aspects of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various aspects of the present disclosure relate to inductive identification systems. An inductive identification system may include an inductive detector (e.g., a detector having one or more conductive coils and associated processing circuitry for receiving and processing inductance signals generate with the coils) and one or more objects having inductive identifiers (e.g., one or more patterned conductive structures in which the pattern includes coded identification information for the object). According to various embodiments, inductive identification systems may be provided in medical systems such as infusion pump systems or drug tracking systems, retail product tracking systems, shipping container tracking systems, or other systems in which objects having inductive identifiers can be detected, identified, and tracked.

Figure 1A:
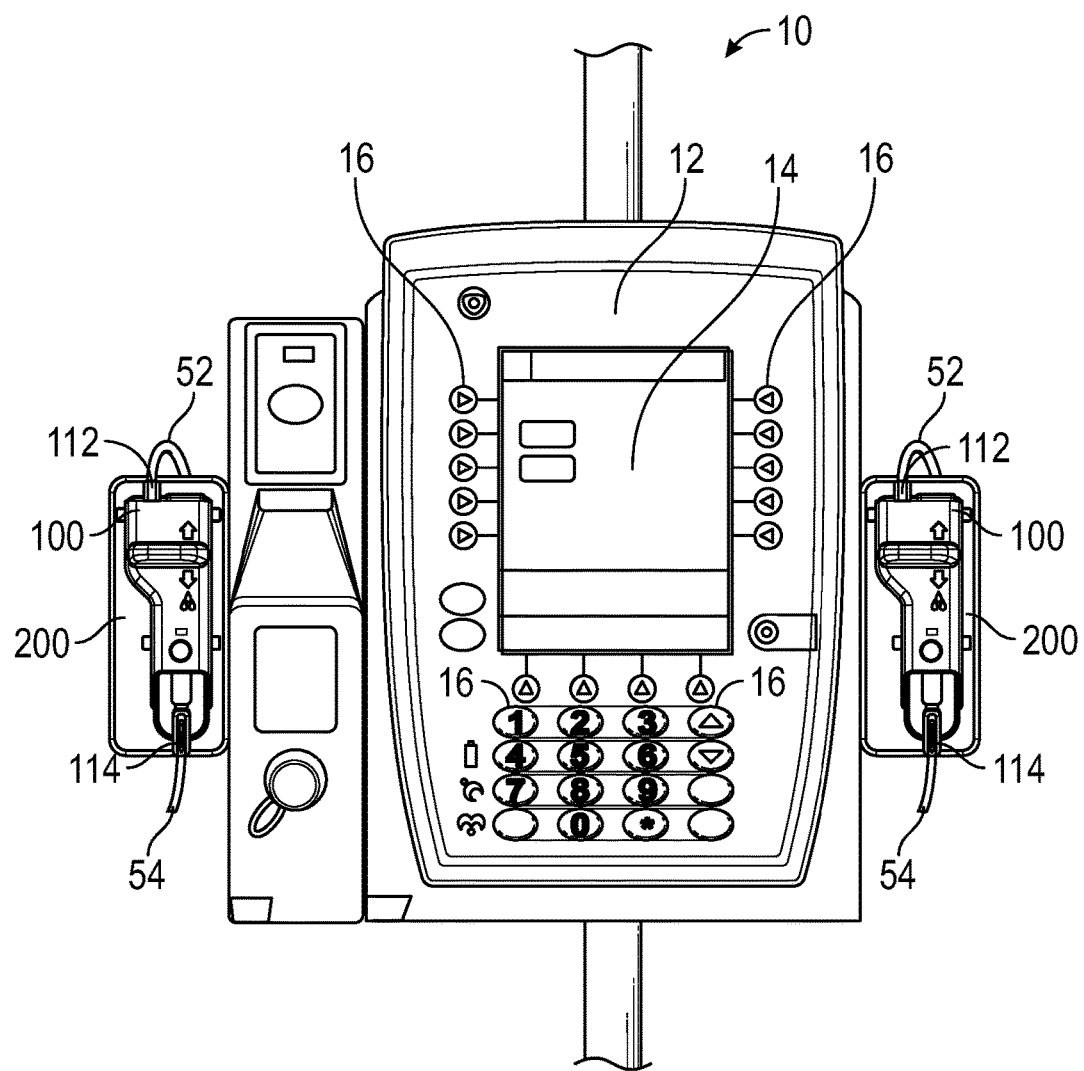
FIGS. 1A and 1B are overview diagrams illustrating examples of infusion pump systems, in accordance with aspects of the present disclosure.

FIG. 1A illustrates an example of an infusion pump system that can contain an embodiment of an inductive identification system. It is to be understood that this is only an exemplary infusion pump system, and an inductive identification system can be utilized in any type of infusion pump system and/or in various other systems as discussed herein. The infusion pump system will be generally explained in reference to FIGS. 1-3. An exemplary infusion pump system 10 may include central processing unit 12 with display screen 14 (e.g., touchscreen display), and data input features 16, for example, a keypad and a series of configurable buttons 16 adjacent to display screen 14. Other types of input and output devices may be used with central processing unit 12 and infusion pump system 10. In certain aspects, central processing unit 12 is operatively coupled to one or more interface modules, with cassette recesses 200, to control and communicate with various operational interfaces thereof.

Figure 1B:
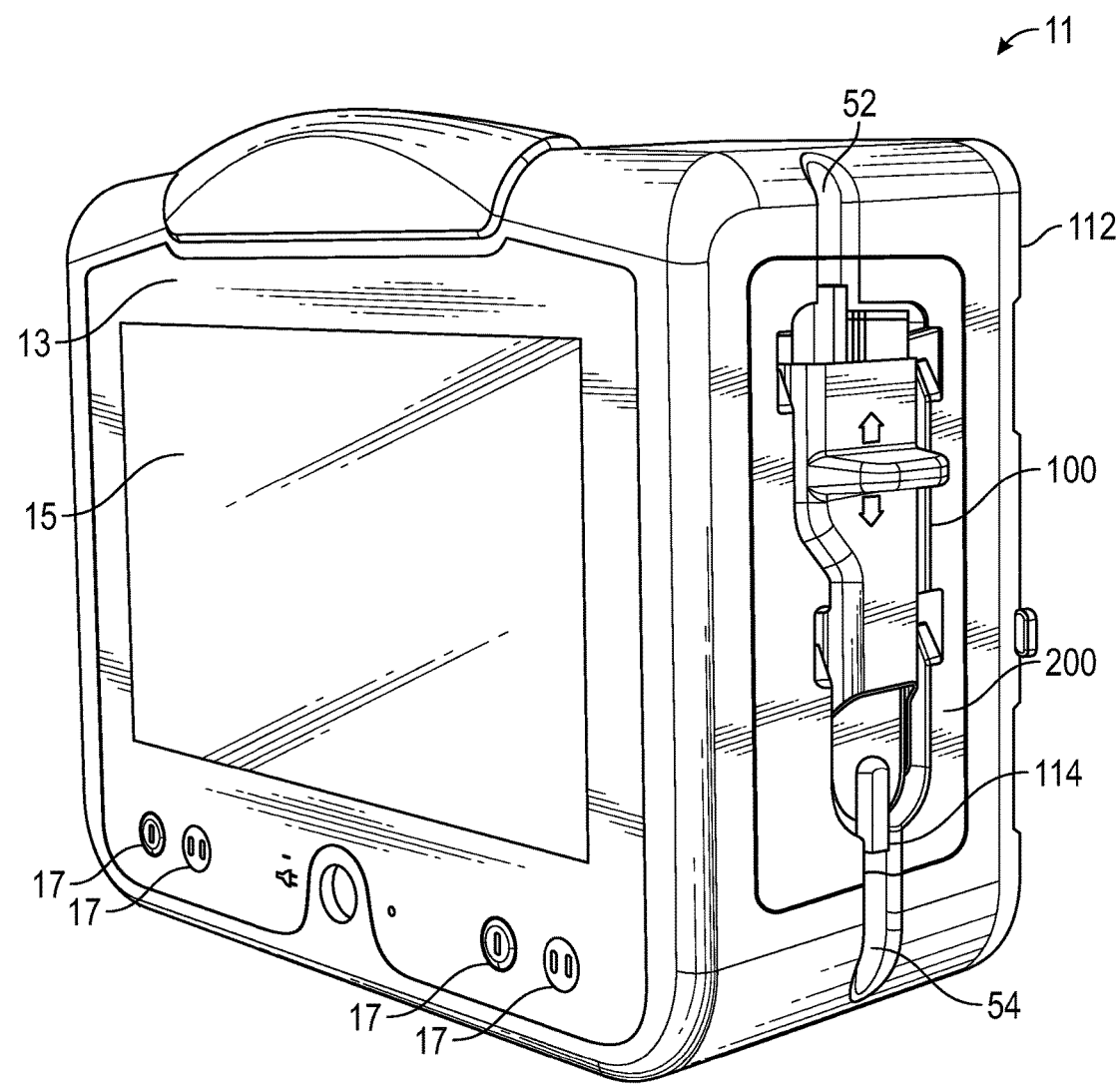

FIG. 1B illustrates another example of an exemplary infusion pump system. This exemplary infusion pump system 11 may include one or more cassette recesses 200 and disposable IV pump cassettes 100. For example, cassette recess 200 may be configured to receive cassette 100 and provide various mechanical couplings and operational interfaces (e.g., fittings, motor, gearing, driveshaft, sensors, etc.). Infusion pump system 11 may include central processing unit 13 with display screen 15 (e.g., touchscreen display), and data input features 17, for example, a series of configurable buttons adjacent to display screen 15. In some implementations, the display screen 15 may provide a keypad or similar data entry feature. Other types of input and output devices may be used with central processing unit 13 and infusion pump system 11. In certain aspects, central processing unit 13 is operatively coupled to one or more interface modules, with cassette recesses 200, to control and communicate with various operational interfaces thereof.

In operation, an IV bag, syringe or other fluid source 52 may be fluidly connected to inlet 112 of cassette 100, and outlet 114 of cassette 100 may be fluidly connected to a patient 54 as shown in the examples of FIGS. 1A and 1B.

Cassettes 100 may comprise a DEHP and Latex-free fluid pathway suitable for various patient populations (e.g., neonate, pediatric, and adult).

In operation, a user (e.g., a caregiver) may obtain a new disposable IV cassette 100 and prime cassette 100 before inserting cassette 100 into cassette recess 200. The caregiver may check for any visible air bubbles in the fluid pathway and may press on any accessible fluid reservoirs (e.g., pressure dome chambers) to move fluid through the cassette 100. Cassette 100 can be securely held and inserted into cassette recess 200 by a single hand of a caregiver. In this regard, caregiver's other hand can be freed to perform other tasks.

FIGS. 2A and 2B illustrate examples of a disposable IV pump cassette 100 and corresponding cassette recess 200 of an interface module. In accordance with certain embodiments, cassette 100 may comprise a cassette body 110 and a slider 170. Cassette 100 may include certain may include certain visual indicators related to operation aspects of the cassette and the infusion pump system in general. For example, cassette may include identifiable images such as fluid drops 171 indicating a position of slider 170 for free-flow (e.g., with a flow stop valve in an open position) and a patient figure 173 proximal to outlet 114. In accordance with some aspects, one or more cassette-seated sensors may be disposed within the cassette recess 200 so as to inform central processing unit 12 that the cassette is locked or secured into place within the cassette recess 200 or seat. For example, cassette recess may include an inductive detector 204 such that an inductive cassette identifier 102 (FIG. 3) can be inductively detected to identify the cassette that has been mounted in cassette recess 200.

Cassette identifier 102 may include one or more features 131 that include coded information such as, but not limited to, a manufacturer, type, and use parameters of cassette 100. Moreover, cassette identifier 102 may be disposed on a top half of the exterior surface of interface-facing frame portion 116 with respect to gravity during use. Thus, a bottom half of the exterior surface of interface-facing frame portion 116 can be reserved for pump drive assembly and flow stop valve features, in accordance with certain embodiments.

As shown in FIG. 1B, inductive detector 204 may include a plurality of conductive coils 231 configured to detect the size, shape, composition, density, or other aspects of features 131 of cassette identifier 102 when cassette 100 is installed in cassette recess 200. Dedicated processing circuitry (not shown) for inductive detector 204 may be provided to extract inductance values (or inductance change values) from, for example, the current in each coil. For example, the presence of a feature of a particular size, shape, or composition may change the inductance of the coil in a predictable and measurable way (e.g., by changing the amount of a current already flowing in the coil or by inducing a current in the coil). The dedicated processing circuitry and/or central processing unit 12 may be used to determine the size, shape, composition, density, or other aspects of features 131 based on the inductance values and to identify, for example, the cassette and an associated IV set based on the determined size, shape, composition, density, or other aspects.

IV Disposable infusion sets may be categorized by therapy. For example, a syringe IV set may be used for neonatal intensive-care unit (NICU) procedures, an epidural IV set may be used to provide anesthesia, an oncology IV set may be used to provide chemotherapy (e.g., in a cancer ward or other cancer treatment setting), a large volume infusion IV set may be used to provide IV drugs in an emergency room (ER), operating room (OR), intensive care unit (ICU) or other procedure. Each IV set has different features that are relevant to the associated therapy and may be identified by inductive detector 204 based on the pattern of features 131 of inductive identifier 102.

Figure 3:
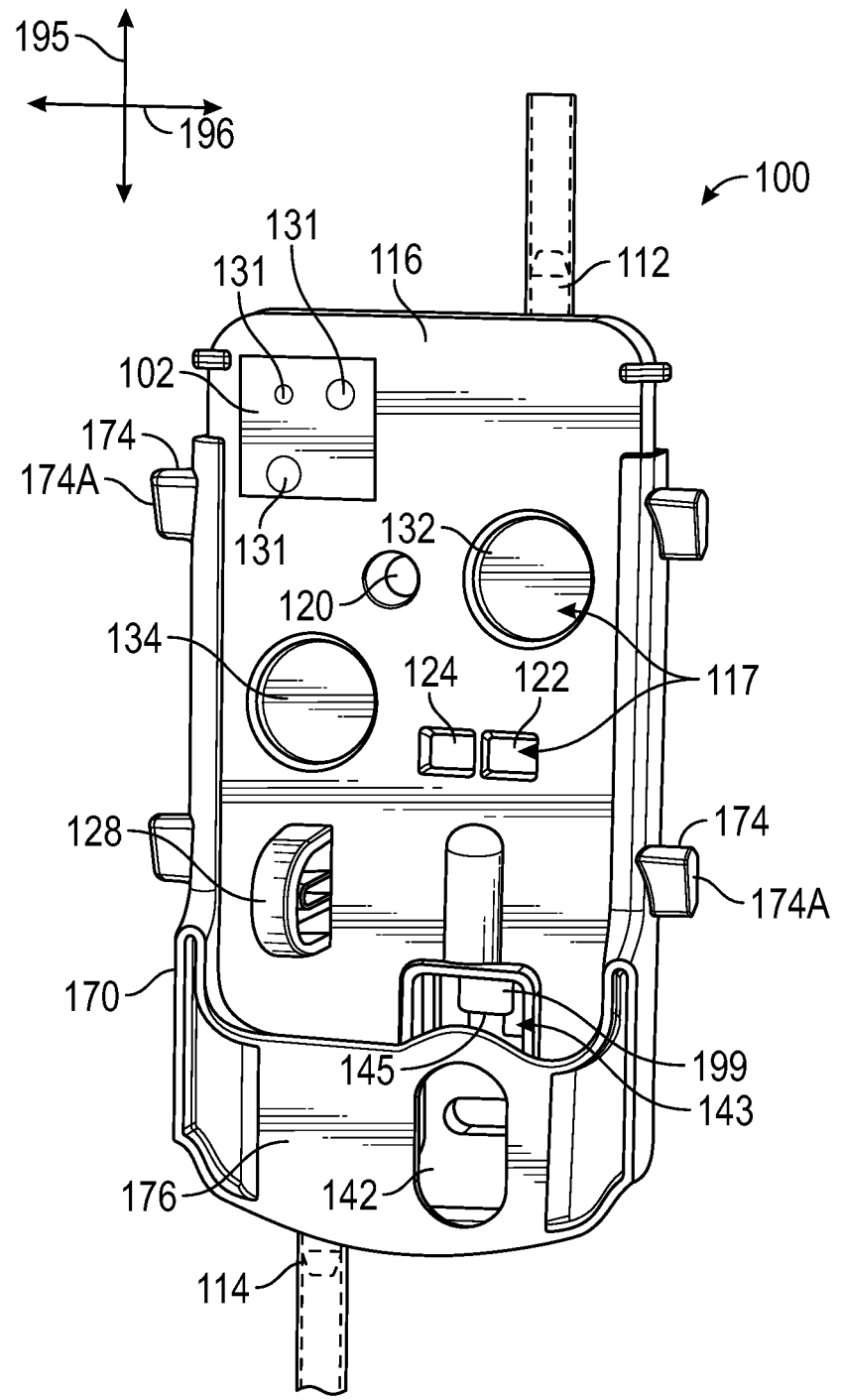
FIG. 3 illustrates a perspective view of the example embodiment of the disposable IV pump cassette of FIGS. 2A and 2B, in accordance with aspects of the present disclosure.

In the example of FIGS. 2B and 3, three coils 231 are provided with inductive detector 204 for detecting the various aspects of three corresponding features 131 of inductive identifier 102. In one example, one aspect of each feature 131 may be detectably varied between three predetermined states to provide 27 distinct identifiers. For example, as shown in the example of FIG. 3, three features 131 are provided in three distinct sizes. Coils 231 may be configured to determine the size of each feature and to identify cassette 100 based on the detected sizes. However, this is merely illustrative. In various other embodiments, as described in further detail hereinafter, the size of each feature 131 may be varied between more than three predetermined sizes, the size of each feature 131 may be varied between less than three predetermined sizes, more than three features 131 may be provided, fewer than three features 131 may be provided, and/or various other aspects of each feature such as the density or composition may be detectably varied between one, two, three, or more than three detectably distinct states to provide any suitable number of distinct identifiers.

As will be discussed in further detail in connection with FIGS. 7-18, inductive identifier 102 may be formed from an inductive identifier film (e.g., a film formed from one or more metal layers and one or more insulating layers such as polymer layers having one or more features such as openings or recesses formed in the metal layer or an insulating layer) or from deposited material (e.g., conductive ink) deposited on a surface of cassette 100 or on a support film configured for attachment to the cassette. An inductive identifier film may be formed from, in one example, a metalized polyethylene terephthalate (PET) film having one or more features such as openings or recesses formed in a metal layer or an insulating layer. In other examples, an inductive identifier film may be formed from a polypropylene (PP) film, a polyethylene (PE) film, or other films that can be heat fused with a polycarbonate (PC) copolymer, a methacrylate-acrylonitrile-butadiene-styrene (MABS) copolymer or with other materials having a substantially similar melting point as PC or MABS copolymers, in which the film includes one or more features such as openings or recesses formed in a conductive layer or an insulating layer to set the inductive properties of the film.

Slider 170 can be fixably and slidably engaged with cassette body 110 such that slider 170 may articulate longitudinally with respect to cassette body 110, but will be constrained within range of sliding motion such that the slider remains coupled to the cassette body 110. Slider 170 may be formed from rigid plastic or polymer material and is clear or translucent in accordance with certain embodiments. In some embodiments, slider 170 may be polycarbonate. In accordance with certain aspects, slider 170 may be lockable at one or more positions, and may include a slider grip 172 for unlocking and articulating slider 170. Slider 170 may also include a plurality of protrusions 174 or lugs that are configured to mate and be releasably lockable with a plurality of slots 274 of the cassette recess 200 (e.g., L-shaped locking channels).

Each of the plurality of protrusions 174 may also comprise a flat face portion 174a that is configured to interface with a respective flat face ramp portions 274a of the cassette engagement slots 274. In this regard, cassette 100 can be self-guided and self-latched into the cassette recess 200.

Accordingly, a door or lever action is not required in order to retain the cassette 100 within the cassette recess 200.

Additionally, an overall size of cassette 100 and cassette recess 200 may be reduced, in accordance with some aspects. For example, in certain embodiments, cassette body 110 may extended longitudinally a length between 70 mm and 90 mm. For orientation reference with respect to the various views of the examples illustrated of FIGS. 2A and 2B, longitudinal axis or y-axis 195 and latitudinal axis or x-axis 196 are provided as a reference on FIG. 3.

Various types, placement, and orientations of the plurality of protrusions 174 disposed on slider 170 are contemplated in the present disclosure. Aspects of the various cassette-coupling techniques illustrated in the example cassette embodiments described herein may be further combined and arranged into additional configurations suitable for specific implementations given the benefit of the present disclosure.

Cassette body 110 may comprise interface-facing frame portion 116 and slider-facing base portion (not shown) with membrane 117 disposed substantially therebetween. Portions of membrane 117 may extend through or be accessible from some openings of frame portion 116 (e.g., upstream pressure dome 132, downstream pressure dome 134, inlet-side valve 122, and outlet-side valve 124). In accordance with certain embodiments, membrane 117 can be a compliant material co-molded to the frame portion 116 and sealingly engaged with the base portion for defining a fluid pathway through cassette body 110 from inlet 112 to outlet 114. Mating edges of frame portion 116 and base portion may be connected by fusing, welding, gluing, or the like. Membrane 917 and the base portion may further define a plurality of other features, some of which may be accessed through openings in frame portion 116.

Frame portion 116, membrane 117, and/or the base portion may define features in or along the fluid pathway, in accordance with certain embodiments. For example, beginning from inlet 112, the fluid pathway may include features such as, but not limited to, upstream pressure dome 132 (e.g., an inlet-side compliant reservoir), inlet-side valve 122, outlet-side valve 124, a pump chamber formed between valves 122 and 124, downstream pressure dome 134 (e.g., an outlet-side compliant reservoir), fluid pathway extension member 128, and a flow stop valve. Other features that are not in or along the fluid pathway, but are disposed on cassette body 110, may include positioning port 120 configured to receive cassette alignment protrusion 220.

In accordance with certain embodiments, membrane 117 may be formed from a thermoplastic elastomer (TPE). Characteristics of certain TPEs can enable effective co-molding with other materials, for example, polycarbonate. Accordingly, in some embodiments, membrane 117 may be co-molded to frame portion 116 and striker 181 may be co-molded to a portion of membrane 117 defining a flow stop valve 164. However, in some embodiments, membrane 117 can be formed from silicon, a silicon-based compound, an elastomeric material suitably compliant for fluid flow, or the like.

In accordance with certain embodiments, interface-facing frame portion 116 and a slider-facing base portion may be formed from a rigid plastic such as, but not limited, a polycarbonate. Additionally, the rigid plastic of frame portion 116 and the base portion may be clear or translucent. The material of membrane 117 (e.g., TPE or other compliant material) and rigid plastic slider 170 may also be clear or translucent, thereby allowing a user or caregiver to readily observe fluid passage through a substantial portion of the fluid pathway of cassette body 110. In some embodiments, the fluid pathway portion of cassette body 110 will be clear or translucent, and other portions will be frosted so as to direct a user or caregiver's attention to the fluid pathway.

In some implementations, slider 170, the base portion, and membrane 117 may be clear or translucent (or at least some portions along the fluid pathway), and the frame portion 116 may not be translucent. For example, the frame portion 116 may be colored in a manner so as to contrast against a color or tint of the fluid expected to be used with cassette 100. In some embodiments, a lens area may be disposed on the base portion alternatively, or in addition to, a lens area disposed on slider 170 to facilitate viewing of the fluid.

Pump drive interface 142 and pump actuator 242 may be configured as a reciprocating motion mechanism (e.g., a scotch-yoke configuration, a cam-driven (perpendicular motion) configuration, a linear actuator, a rotary actuator, etc.) in certain implementations. In such implementations, pump drive interface 142 may include opposing ramp portions for guiding a rotatable pin 252 of pump actuator 242 toward a slot of pump drive interface 142. The opposing ramp portions may allow self-alignment of the piston 145 to the pump interface pin 252. For example, the outer edges of the opposing ramp portions may be arranged at a distance that will ensure engagement with the rotatable pin 252 of pump actuator 242. When the rotatable pin 252 contacts one of the ramp portions, the pump drive interface 142 will move the piston to align the elongate slot of pump drive interface 142 with the rotatable pin 252 of pump actuator 242. However, it is to be appreciated that other pump drive assemblies are contemplated with cassette 100 and cassette recess 200 in accordance with the present disclosure. Actuator-receiving portion 142 may be accessible by pump actuator 242 via an aperture through interface-facing sider section 176

Piston 145 may be driven by a force provided by pin 252 against the sidewall surfaces of the elongate slot as pump actuator 242 rotates. The elongated configuration of the slot may allow pin 252 to reciprocate back and forth along the elongated dimension of the slot without providing a force on piston 145 in that direction as the pin provides a perpendicular force for actuating piston 145 within piston barrel 199. However, other configurations of a slot in interface 142 may be provided to generate various pumping characteristics with a rotating pin 252.

In some embodiments, pump drive assembly may be configured to produce a 3.5 mm piston stroke for operation with a pump chamber configured to be a 10 mm outer diameter reservoir. Moreover, the pump drive assembly may be arranged below the pump chamber, in accordance with some embodiments.

In certain embodiments, cassette recess 200 may include an upstream pressure sensing probe 232 and downstream pressure sensing probe 234 enabling measurement of in-line pressure and fault isolation to a section of the fluid pathway. For example, upstream pressure sensing probe 232 may operably contact upstream pressure dome 132 through a corresponding opening of interface-facing frame portion 116. Similarly, downstream pressure sensing probe 234 may operably contact downstream pressure dome 134 through a corresponding opening of frame portion 116.

One or more fluid sensors may be disposed within sensor slot 228. The one or more fluid sensors disposed within sensor slot 228 can be ultrasonic sensors configured as an air-in-line detector, for example. In certain embodiments, extension member 128 may be disposed on cassette body 110 and positioned along the fluid pathway between downstream pressure dome 134 and a flow stop valve. However, in some embodiments, extension member 128 can be positioned at other locations along the fluid pathway such as, but not limited to, between inlet 112 and upstream pressure dome 132. Additionally, in other embodiments, a plurality of extension members 128 with a plurality of corresponding sensor slots 228 may be positioned along a fluid pathway of cassette body 110.

Cassette body 110, or a substantial portion thereof, may extend a depth of between 6 mm and 8 mm. Fluid pathway extension member 128 (see FIG. 3) may further extend between 8 mm to 10 mm. In certain aspects, the slider grip 172 of slider 170 may extend between 10 mm to 14 mm from cassette body 110. It is to be appreciated that the process of cleaning of inlet recess 212, outlet recess 214, and cassette recess 200 is made efficient in the shallow recess configuration in accordance with certain embodiments should any fluid or debris accumulate within cassette recess 200. The shallow recess configuration of cassette recess 200, and associated longitudinal alignment of cassette 100 such that a smaller of volumetric dimensions of cassette 100 (e.g., depth being smaller than length and width in certain embodiments) further enables additional space for arrangement of mechanical couplings and operational interfaces and optimizes the overall space requirements of cassette recess 200 and infusion pump system in general.

For example, a pumping operation of infusion pump system 10, 11 when cassette 100 is primed and seated in cassette recess 200 may comprise activating outlet-side valve actuator 224 such that outlet-side valve 124 is closed or sealed while activating inlet-side valve actuator 222 such that inlet-side valve 122 is opened. Opening of inlet-side valve 122 may coincide with or occur shortly before the start of a reverse stroke of piston 145 (e.g., a movement of piston 145 away from pump chamber). Accordingly, fluid can flow from upstream pressure dome 132 to the pump chamber. Alternatively, or in addition to, outlet-side valve 124 may comprise a one-way valve mechanism that permits flow of fluid under normal conditions in one direction (from a fluid container to a patient). Additionally, in some alternative embodiments, inlet-side valve 122 may also comprise a one-way valve or choke mechanism permitting flow of fluid in primarily one direction (e.g., from a fluid container to a patient) under normal operating conditions. In this configuration, cassette recess 200 may not need to incorporate either outlet-side valve actuator 224 or inlet-side valve actuator 222. Outlet-side valve 124 and inlet-side valve 122 may limit flow of fluid in one direction, but permit flow in an opposite direction in the event fluid pressure overcomes a cracking pressure of the valves.

Continuing with the valve-operated implementation, pumping operation may comprise activating outlet-side valve actuator 224 such that outlet-side valve 124 is open while activating inlet-side valve actuator 222 such that inlet-side valve 122 is closed or sealed. Opening of outlet-side valve 124 may coincide with or occur shortly before a start of a forward stroke of piston 145 (e.g., a movement of piston 145 toward the opening/access 125 of the pump chamber such that the volume of the pump chamber is reduced). Thus, fluid can flow from pump chamber down the fluid pathway to outlet 114.

In certain embodiments, the upstream pressure dome 132 may be smaller than the downstream pressure dome 134 to minimize retained volume. Likewise, the downstream pressure dome 134 may be larger than the upstream pressure dome 132 to improve resolution of fluid pressure thereby allowing for an accurate and precise volume of fluid to be pumped and any upstream or downstream pressures to be accurately measured.

Pump drive interface 142 can be operatively coupled to piston 145 slidably engaged within piston guide 143 and/or casing 199 (e.g., a generally cylindrical and/or frustoconical piston barrel) such that reciprocal movement of piston 145 within a pump chamber formed in part by the piston barrel 199 provides a moving seal that defines the edge of the pump chamber to urge fluid through the fluid pathway of cassette body 110.

When cassette 100 is installed in cassette recess 200, identifier 102 may be disposed in proximity (e.g., within a proximal distance that is less than half of the diameter of the smallest of coils 231 of detector 204) to detector 204 so that one or more features 131 may be detected by their inductive effect on detector 204. As shown in FIG. 2B, one or more reference coils 231R may be provided in cassette recess 200 (e.g., interior to or embedded within housing structure 216 of the cassette recess) that are located away from the location at which identifier 102 is disposed when cassette 100 is inserted in cassette recess 200. Reference inductance values may be captured using reference coil 231R during manufacturing and during identification operations for cassette 100. Differences in the reference inductance values captured during manufacturing and during identification operations may be used to correct inductance measurements captured by coils 231 during identification operations (e.g., to correct for temperature variations in the environment of the system during various measurement/identification operations). In this way, coils 231 may be provided with the ability to inductively detect relative and/or absolute aspects of each feature 131 in various operating environments.

Figure 4:
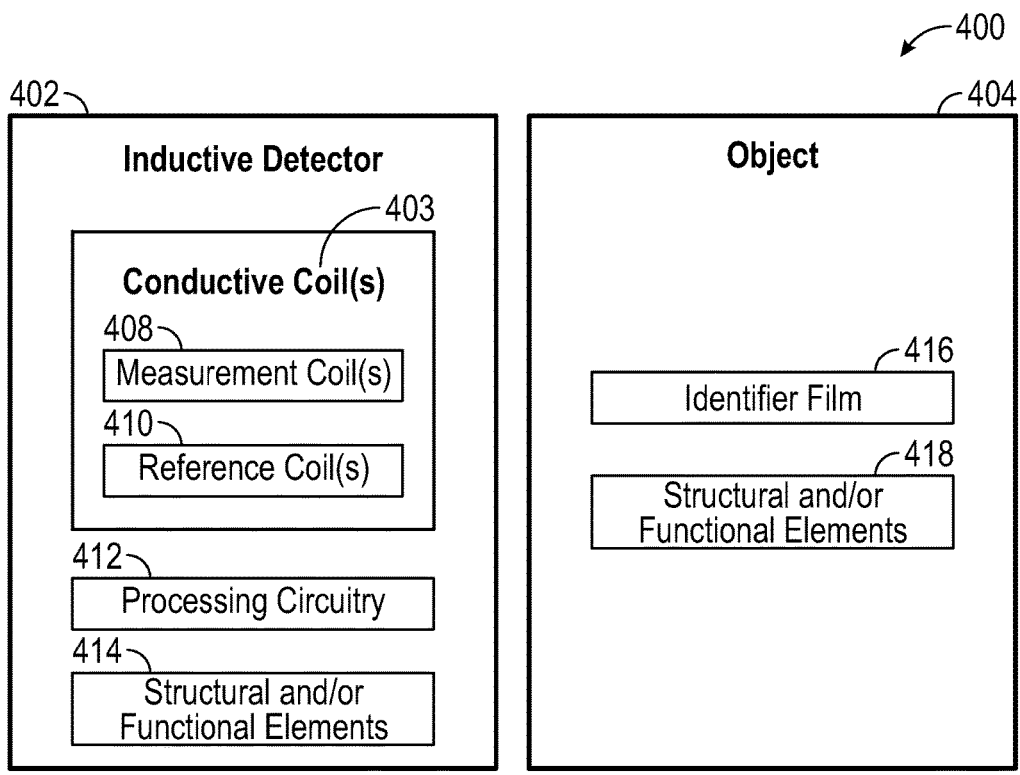
FIG. 4 illustrates a block diagram of an example embodiment of an inductive identification system having an inductive detector and an object having an inductive identification film, in accordance with aspects of the present disclosure.

Although identification of IV sets by inductive identification of a cassette placed in a cassette recess of an infusion pump system are sometimes discussed herein as an example, it should be appreciated that inductive object identification can be implemented for various other types of systems. FIG. 4 is a block diagram illustrating a system 400 having an inductive detector and an object having an inductive identifier.

As shown in FIG. 4, system 400 may include inductive detector 402 and one or more objects such as object 404 having an inductive identifier such as identifier film 416. Identifier film 416 may, for example, be implemented as identifier 102 of a cassette for an infusion pump system or may be implemented as an identifier for another object. For example, object 404 may be consumer product such as a grocery item, a clothing item, a hardware item, an electronic device, a household item, an automotive item, or the like. Identifier film 416 may be attached to or integrally formed with, for example, packaging of the object or the object itself. For example, identifier film 416 may be a patterned conductive film that is attached to a shampoo bottle for tracking of the production, sales, shipping, and/or usage of the specific bottle, a type of shampoo in the bottle, or a brand of shampoo (as examples). In the example in which object 404 is a consumer product, inductive detector 402 may be implemented as a product scanner at a warehouse, a manufacturing facility, a retail location, or any other location at which it may be desirable to identify the location, type, brand, or other aspect of the consumer product. In one example, inductive detector 402 may be provided at the checkout stand at a grocery store and configured to use conductive coil(s) 403 (e.g., measurement coil(s) 408) to detect one or more features of identifier film 416.

As shown in FIG. 4, conductive coil(s) 403 may include one or more reference coils 410. Reference inductance values may be captured using reference coil(s) 410 during calibration operations for detector 402. During identification operations in which detector 402 is being used to identify object 404, additional reference values may be gathered using reference coil(s) 410 before, during, and/or after capturing inductance values using measurement coil(s) 408 while identifier film 416 (or another patterned conductive identifier) is in proximity to conductive coils 403. As noted above, one or more features of identifier film 416 may be considered to be in the proximity of a measurement coil 408 when the one or more features are within a perpendicular distance of less than half of the width (e.g., diameter) of the coil. For example, for a coil having a 6 mm diameter, a feature may be within the proximity of the coil if the features is within 3 mm of the coil.

As shown in FIG. 4, inductive detector 402 may include processing circuitry (e.g., one or more processors, integrated circuits, volatile or non-volatile memory, etc.) for extracting inductance values from coils 403 and for extracting identifying information for an object based on the extracted inductance values. For example, processing circuitry 412 may store a look-up table of inductance values, corresponding feature aspects, and corresponding object information from which the object information can be obtained when a particular set of inductance values or a particular pattern of features is identified. As shown, object 404 may include structural and/or functional elements 418 such as a housing, packaging, electronic devices, or other structure and/or functional elements according to various embodiments. For example, in one embodiment, structural and/or functional elements 418 may include a food package and the food inside the food package. In another embodiment, structural and/or functional elements 418 may include a housing of a cassette such as cassette 100 and the fluid pathways, valves, and pump components therein.

Inductive detector 402 may include structural and/or functional elements 414 such as a housing, packaging, electronic devices, or other structure and/or functional elements according to various embodiments. For example, in one embodiment, structural and/or functional elements 414 may include a conveyor belt of a grocery checkout stand, a detector housing, and additional processing circuitry such as checkout, payment, and/or inventory circuitry. In another embodiment, structural and/or functional elements 414 may include a housing of a infusion pump system 10, a cassette recess, and alignment, valve operation, and pump drive components therein. Although the inductive identifier of object 404 is shown as an identifier film, it should be appreciated that other conductive materials such as conductive ink may be used to form a patterned conductive identifier for object 404 that can be scanned or read based on inductance values obtained by detector 402.

Figure 5:
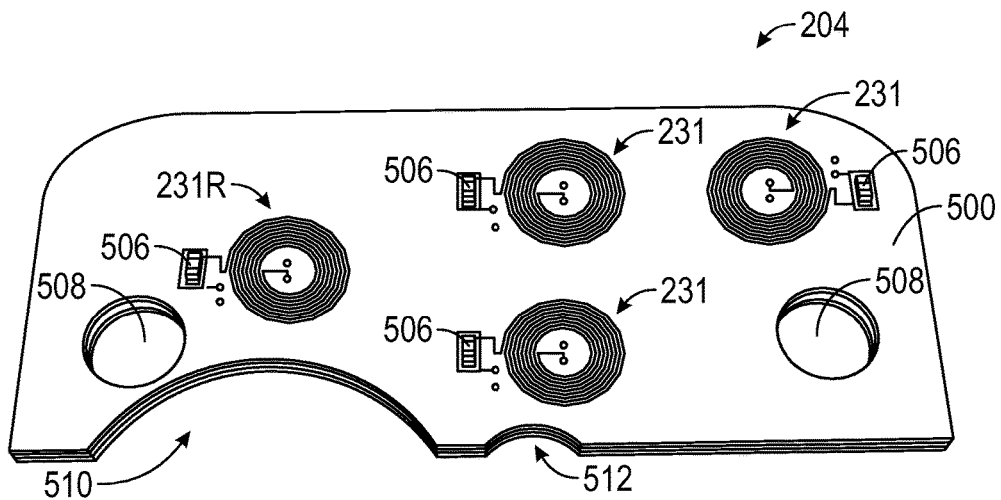
FIG. 5 illustrates a perspective view of an example embodiment of an inductive detector board having a plurality of conductive coils, in accordance with aspects of the present disclosure.

FIG. 5 shows an example implementation of a portion of inductive detector 204 as described herein. As shown in FIG. 5, inductive detector 204 may include a board 500 (e.g., a single or multi-layer printed circuit board or flexible printed circuit) on which conductive coils 231 and reference coil 231R may be formed. Conductive coils 231 and 231R may be formed on a surface of board 500 or may extend to one or more layers of depth within board 500. Control and/or readout circuitry 506 may be disposed on board 500 and coupled to each coil 231 (e.g., for driving a current in the coil, for measuring an induced current in the coil, or for measuring inductance values or inductance change values associated with each coil). Additional processing circuitry (not shown) may be coupled to control and/or readout circuitry 506 and may receive inductance values or corresponding pattern feature values from control and/or readout circuitry 506 for further processing.

Figure 6:
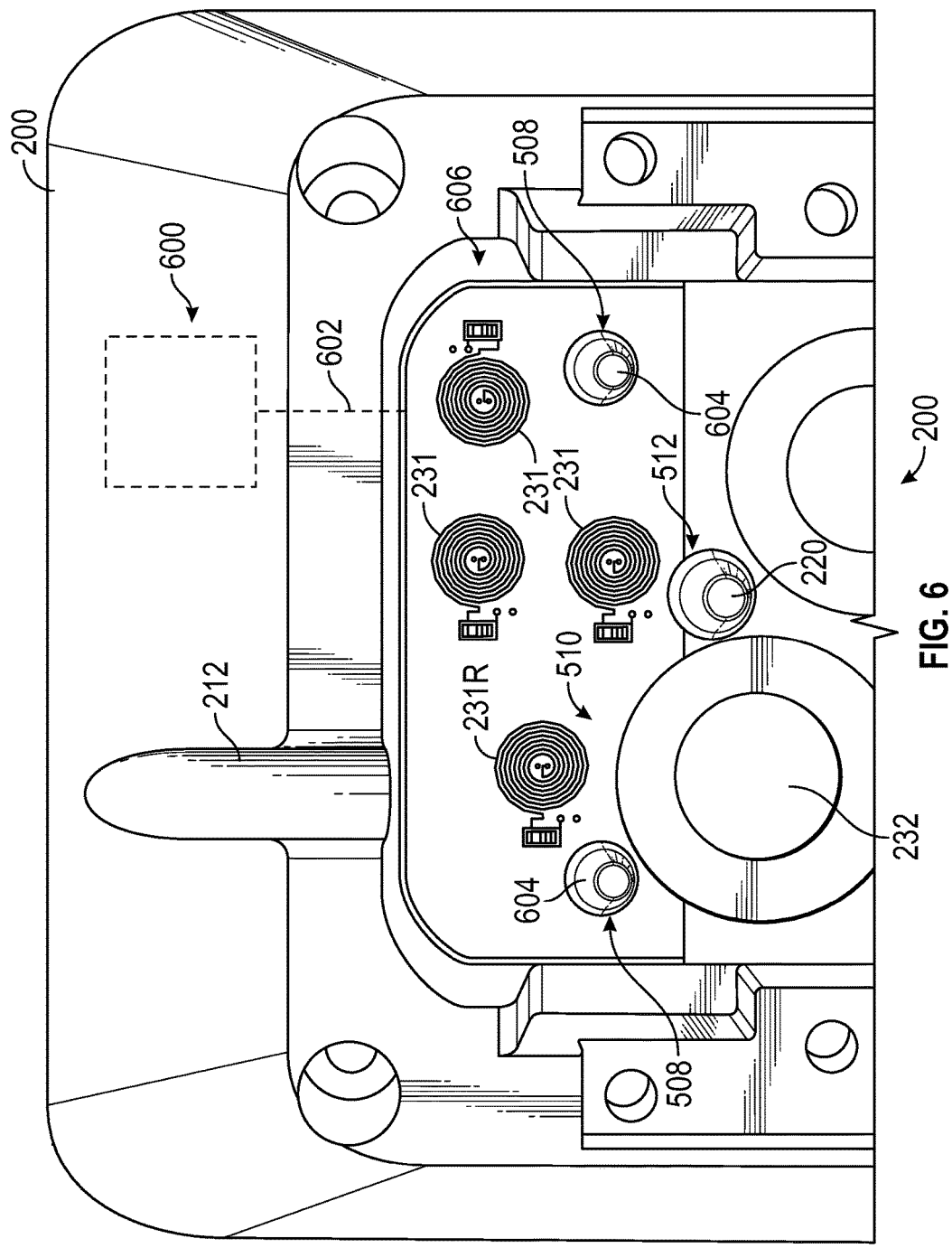
FIG. 6 illustrates a perspective view of an example embodiment of a cassette recess implemented with the inductive detector board of FIG. 5, in accordance with aspects of the present disclosure.

Board 500 may have one or more features such as openings 508 and cutouts 510 and 512 that help align and accommodate installation of board 500 in another device such as in cassette recess as shown in FIG. 6. In the example of FIG. 6, openings 508 of board 500 may receive alignment protrusions 604 disposed within a detector recess 606 within cassette recess 200. In this way, when board 500 is placed into detector recess 606, cutout 510 may accommodate upstream pressure sensing probe 232 and cutout 512 may accommodate cassette alignment protrusion 220. Additional processing circuitry such as processor 600 may be provided within cassette recess 200 for receiving inductance values from coils 231 and/or 231R (e.g., along a conductive path 602), for processing inductance values to identify a cassette/IV set type, and/or to provide control signals such as current control signals to coils 231.

Each of coils 231 may be aligned, when cassette 100 is installed in cassette recess 200, with a particular feature 131 of inductive identifier 102 of cassette 100. As shown in FIG. 7, features 131 may be circular features each having a radius (or corresponding diameter) such as radii RA, RB, and RC. The example shown in FIG. 7 in which RC>RB>RA may represent one possible combination of features that corresponds to a particular cassette/IV set type. For example, other combinations such as (RA=RB=RC, RA>RB>RC, RA=RB>RC, RA<RB=RC, etc.) may each correspond to a distinct cassette/IV set type. However, this is merely illustrative. In various embodiments, other variations in the features of identifier 102 may be used to identify a particular object such as a cassette/IV set type.

As shown in FIG. 8, a single feature 131 (e.g., a single circular feature or other shaped feature such a square feature, a rectangular feature, or an asymmetric feature) may be provided with a varying absolute size that can be used to identify the feature (e.g., a radius R1 may correspond to a first cassette/IV set type and a radius R2 may correspond to a second, different cassette/IV set type).

Figure 10:
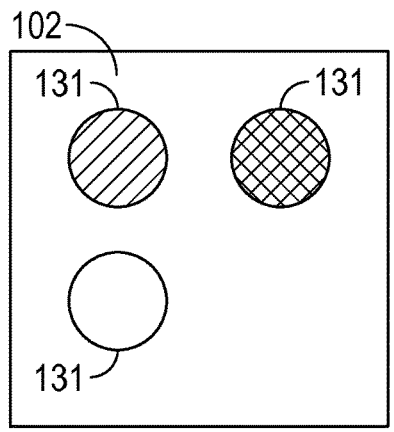
FIG. 10 illustrates a top view of an example embodiment of an inductive identifier film having various features formed from various materials, in accordance with aspects of the present disclosure.

As shown in FIG. 9, each feature 131 may include multiple sub-features such as a conductive annulus 900 surrounding an insulating core 902. As shown in FIG. 10, various features 131 may be formed with a common size (e.g., circular features with a common diameter) and formed from one or more different respective materials. The difference in the inductance effect on coils 231 of the various materials may be detected and used to recognize a particular pattern of materials that is known to correspond to, for example, a particular cassette/IV set type. The features 131 formed from different materials in the example of FIG. 10 may also be formed with different sizes and/or shapes to provide additional distinguishing features for coded identification.

Figure 11:
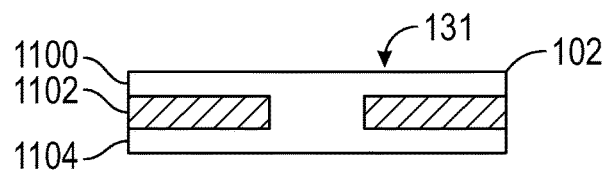
FIG. 11 illustrates a cross-sectional view of an example embodiment of an inductive identifier film having a feature formed from an opening that extends through one of a plurality of layers, in accordance with aspects of the present disclosure.

FIG. 11 is a cross sectional side view of a portion of a cassette identifier 102 formed from a multilayer film. As shown in the example of FIG. 11, a feature 131 may be formed from a conductive material 1102 (e.g., aluminum) that is disposed between one or more insulating and/or protective layers such as a top layer 1100 and a bottom layer 1104. As shown, feature 131 may be formed from an opening in conductive layer 1102. The opening in conductive layer 1102 may be partially or completely filled with an insulating material or may be an air gap or a vacuum gap. Layers 1100 and 1104 may, for example, be polymer layers. In one embodiment, the identifier film of FIG. 11 may be formed from a metalized biaxially-oriented polyethylene terephthalate (BoPET) film. The metallization layer, may, for example, include aluminum. In the example of FIG. 11, identifier 102 is formed from a three layer film. However this is merely illustrative. In other embodiments, any suitable number of layers may be provided to enhance and/or tune the inductance effects on coils 231 during detection and identification operations.

Figure 12:
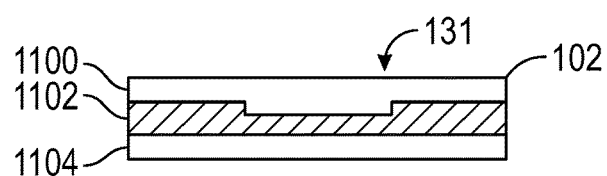
FIG. 12 illustrates a cross sectional view of an example embodiment of an inductive identifier film having a feature formed from an opening that extends partially through one of a plurality of layers, in accordance with aspects of the present disclosure.
Figure 13:
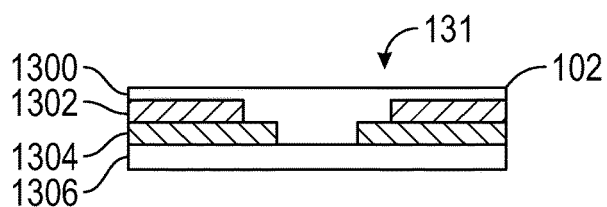
FIG. 13 illustrates a cross sectional view of an example embodiment of an inductive identifier film having a feature formed from openings of various sizes in various corresponding ones of a plurality of layers, in accordance with aspects of the present disclosure.

In the example of FIG. 11, the opening in conductive layer 1102 that forms feature 131 extends completely through the conductive layer from the top polymer layer 1100 to the bottom polymer layer 1104. However, this is merely illustrative. As shown in FIG. 12, features 131 may be formed from a recess in a conductive layer of a film in which the recess extends partially into the conductive layer so that the conductive layer is thinner in the region of the feature than in other regions of the film. As shown in FIG. 13, an identifier 102 formed from a film may include more than one conductive layer. In the example of FIG. 13, identifier film 102 includes a first conductive layer 1302 formed on a second conductive layer 1304. Conductive layers 1302 and 1304 are disposed between polymer layers 1300 and 1306. As shown in FIG. 13, each conductive layer may include an opening that forms a portion of a feature 131. The openings in each conductive layer may have a common size or may be of different sizes as in the example of FIG. 13. Openings and/or recesses as described in connection with FIGS. 11, 12, and 13 may be formed, for example, by laser ablation of the conductive layer before or after the film has been attached to an object to be identified by the film.

Figure 14:
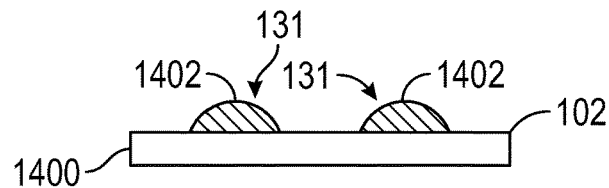
FIG. 14 illustrates a side view of an example embodiment of an inductive identifier formed from deposited features of various sizes, in accordance with aspects of the present disclosure.
Figure 15:
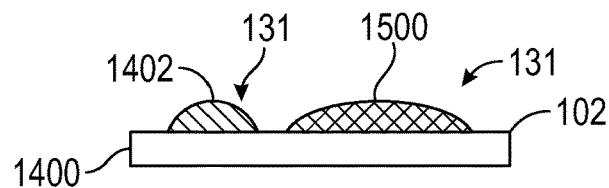
FIG. 15 illustrates a side view of an example embodiment of an inductive identifier formed from deposited features of various sizes and various materials, in accordance with aspects of the present disclosure.
Figure 16:
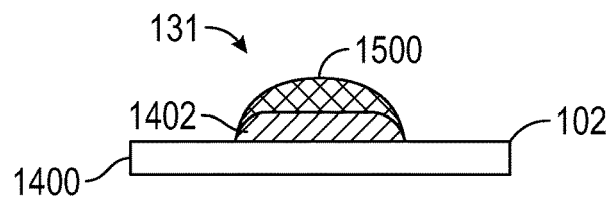
FIG. 16 illustrates a side view of an example embodiment of an inductive identifier formed from deposited features formed from various overlapping materials, in accordance with aspects of the present disclosure.
Figure 17:
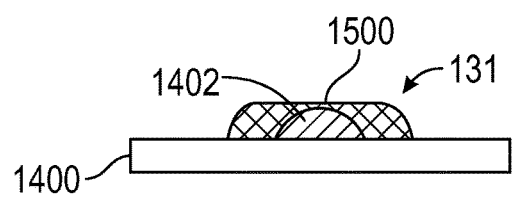
FIG. 17 illustrates a side view of an example embodiment of an inductive identifier formed from deposited features formed from various overlapping materials of various sizes, in accordance with aspects of the present disclosure.
Figure 18:
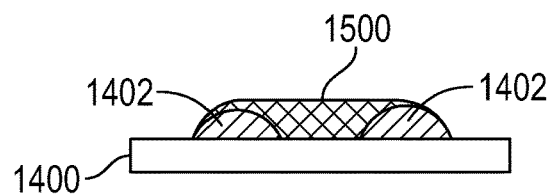
FIG. 18 illustrates a side view of an example embodiment of an inductive identifier formed from deposited features formed from various overlapping materials in which one material is formed at least partially in an opening in another material, in accordance with aspects of the present disclosure.

In some embodiments, an inductive identifier 102 may include features 131 formed from deposited materials as in the examples of FIGS. 14-18. As shown in FIG. 14, features 131 may be formed from deposits of a common material 1402 on a substrate 1400. Substrate 1400 may be a polymer layer configured to be attached to an object to be identified or may be a portion of the object itself or packaging for the object. For example, material 1402 may be a conductive ink that is printed on substrate 1400 to form one or more features 131 such as the features having different sizes and a common material in FIG. 14, features such as the features having different sizes and different materials 1402 and 1500 as in FIG. 15, features formed from multiple different stacked deposited materials 1402 and 1500 having a common size as in FIG. 16, features formed from multiple different stacked deposited materials 1402 and 1500 having different sizes as in FIG. 17, and/or other features from multiple materials. As shown in FIG. 18, material 1500 may be formed over multiple deposits of material 1402. By covering a patterned conductive material 1402 with another conductive material, the pattern of the underlying material 1402 may be obscured from view, thereby increasing the difficulty of copying or counterfeiting the identifier. For example, materials 1402 and 1500 may be formed from conductive inks having different conductivities, different densities, or other different electrical properties, but that appear visually similar so that a potential counterfeiter would have difficulty determining the location of the material 1402 relative to the material 1500.

Figure 19:
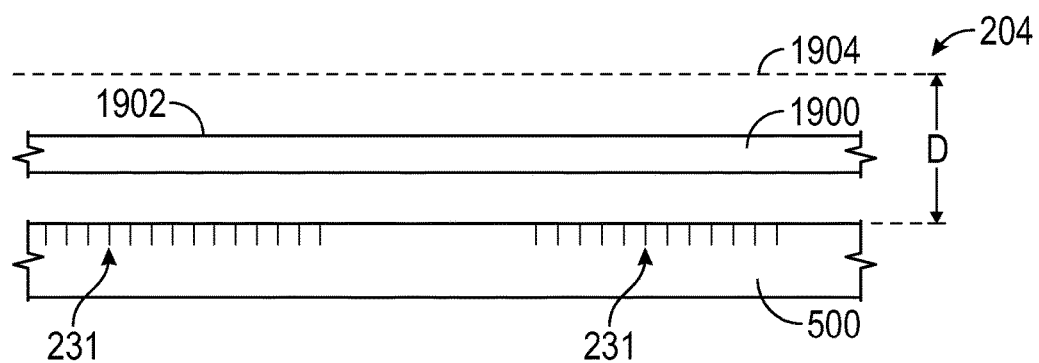
FIG. 19 illustrates a cross-sectional view of an example embodiment of a portion of a cassette recess showing how an inductive detector can be formed behind a housing structure of the cassette recess, in accordance with aspects of the present disclosure.

An inductive detector for detecting the features 131 of an inductive identifier 102 may be formed within a housing of another device or may form a portion of an outer surface of the device. FIG. 19 shows an inductive detector 204 disposed within an outer housing structure 1900 of a device so that the outer housing structure 1900 forms an outer surface 1902 of the device. In the example of FIG. 19, board 500 containing coils 231 is disposed within the housing of the device. For example, housing structure 1900 may be an outer housing structure of cassette recess 200 of infusion pump system 10 and board 500 may be disposed within the cassette recess. Board 500 and coils 231 may be positioned, and the mounting features for mounting the cassette in the cassette recess (e.g., features 174 of cassette 100, features 274 of cassette recess 200, and guide pin 220), may be configured such that, when the cassette is installed in the cassette recess, the inductive identifier of the cassette is located at a position 1904 that is a distance D from coils 231. The distance D may, for example, be a distance of less than approximately half of the width of the coils 231.

Figure 20:
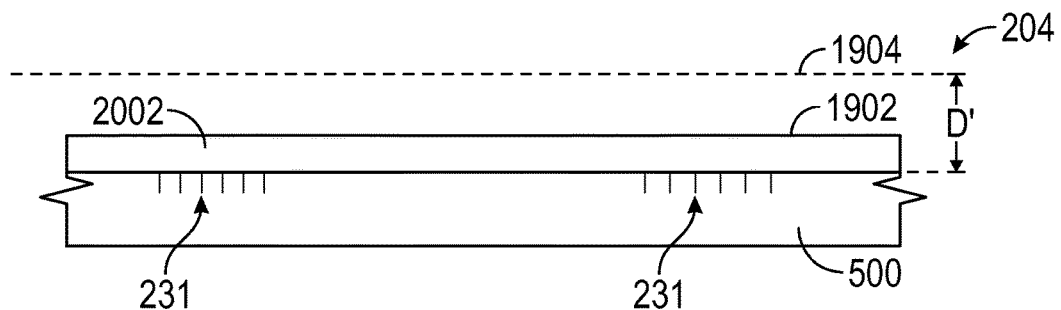
FIG. 20 illustrates a cross-sectional view of an example embodiment of a portion of a cassette recess showing how an inductive detector may include a coating that forms an exterior surface of the cassette recess, in accordance with aspects of the present disclosure.

In order to reduce the tolerances in mounting the cassette in the cassette recess, board 500 may be mounted in the cassette recess 200 such that the board itself forms an outer surface of the cassette recess and no housing structure is interposed between the mounted location 1904 of an identifier film and coils 231 as in the example of FIG. 20. In such a configuration, board 500 may be provided with a protective coating 2002 such as an epoxy coating that is easily cleaned and chemically resistant to facilitate cleaning of the surface of cassette recess 200 without damaging the inductive detector. As shown in FIG. 20, in such a configuration, the mounted location 1904 of an inductive identifier of a cassette, when the cassette is mounted in the cassette recess may be at a distance D' from coils 231. The distance D' may, for example, be a distance of less than approximately half of the width of the coils 231.

Figure 21:
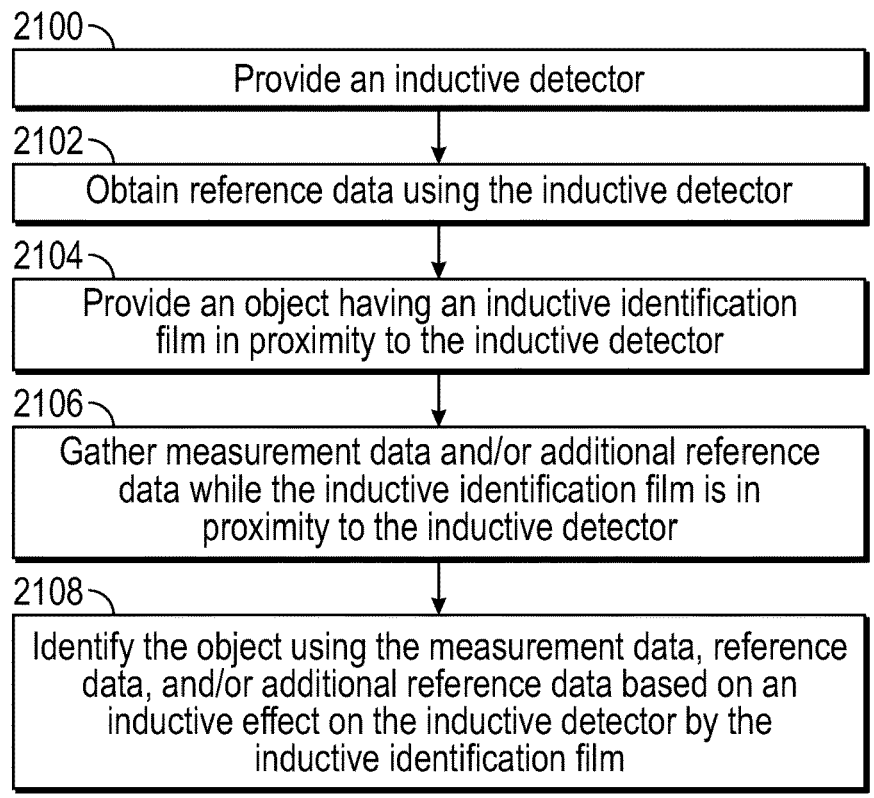
FIG. 21 illustrates a flowchart showing illustrative operations that may be performed for inductive identification of objects, in accordance with aspects of the present disclosure.

Illustrative operations that may be performed for inductive identification of an object are shown in FIG. 21 according to an embodiment.

At block 2100, an inductive detector may be provided. The inductive detector may be a standalone detector or a detector implemented in a larger system such as an infusion pump system or a product scanning system for a retailer, warehouse, shipper, or manufacturer. The inductive detector may, for example, include one or more conductive coils configured as measurement coils and/or reference coils.

At block 2102, reference data may be obtained using the inductive detector (e.g., by gathering and storing inductance values with a reference coil when no metallic or conductive material is in the proximity of the reference coil). The reference data may be obtained, for example, during factory calibration or other manufacturing operations.

At block 2104, an object having an inductive identifier such as an inductive identification film or deposited inductive identifier may be provided in proximity to the inductive detector. For example, a product to be shipped having an inductive identifier film attached to the packaging of the product may be placed on an inductive identifier at a warehouse. In another example, a cassette having a cassette/IV set type inductive identifier may be installed in a cassette recess of an infusion pump system.

At block 2106, measurement data and/or additional reference data may be gathered while the inductive identification film is in proximity to the inductive detector. Gathering the measurement data may include gathering inductance values using the measurement coils of the inductive detector. Gathering the additional reference data may include gathering inductance values using the reference coil of the inductive detector while object is in proximity to the inductive detector, the object being free of metallic and/or conductive materials in the proximity of the reference coil.

At block 2108, the object may be identified using the measurement data, reference data, and/or additional reference data based on an inductive effect on the inductive detector by the inductive identification film. For example, a difference between the reference data and the additional reference data may be used to perform a correction (e.g., a temperature correction) for the measurement data. The corrected measurement data may then be used to identify an inductance pattern that corresponds to a pattern of sizes, shapes, and/or compositions of features of the inductive identifier of the object. The identified pattern of features may be used to identify a corresponding object. For example, a particular pattern of conductive features in the inductive identifier may correspond to a particular IV set/cassette type. A database of known objects and corresponding coded inductive identifier patterns may be stored by the detector or accessible over a network (e.g., at a secure server).

Figure 22:
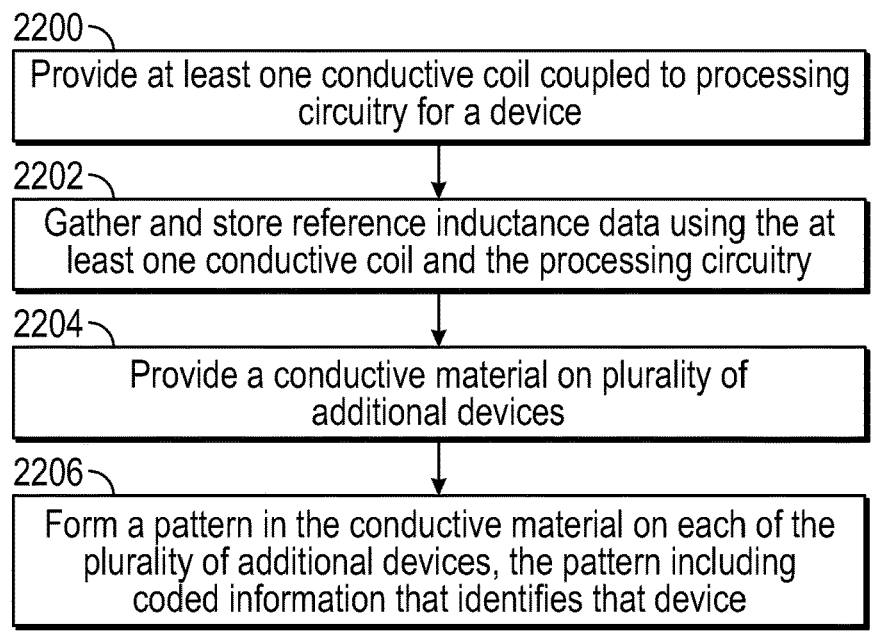
FIG. 22 illustrates a flowchart showing illustrative operations that may be performed for providing an inductive identification system, in accordance with aspects of the present disclosure.

Illustrative operations that may be performed for making an inductive identification system are shown in FIG. 22 according to an embodiment.

At block 2200, at least one conductive coil coupled to processing circuitry for a device may be provided. The at least one conductive coil may include one or more measurement coils and one or more reference coils, each coupled to inductance readout circuitry for that coil.

At block 2202, reference inductance data may be gathered and stored using the at least one conductive coil (e.g., a reference coil) and the processing circuitry. The reference data may be obtained with a reference coil when no metallic or conductive material is in the proximity of the reference coil. The reference data may be obtained, for example, during factory calibration or other manufacturing operations. The reference data may include one or more reference inductance values stored using the processing circuitry for later use during inductive identification operations using the at least one conductive coil.

At block 2204, a conductive material such as a conductive film or a printed conductive material may be provided on plurality of additional devices. The additional devices may include any object for which identification may be desired.

At block 2206, the conductive material may be patterned with a coded pattern that corresponds to identifying information for that device. For example, a specific set of features each having a size, a shape, a composition, or other aspect may be laser encoded in film or patterned during conductive ink printing. The operations of block 2206 may be performed before, during or after the operations of block 2204.

The subject technology is illustrated, for example, according to various aspects described above. Various examples of these aspects are described as numbered concepts or clauses (1, 2, 3, etc.) for convenience. These concepts or clauses are provided as examples and do not limit the subject technology. It is noted that any of the dependent concepts may be combined in any combination with each other or one or more other independent concepts, to form an independent concept. The following is a non-limiting summary of some concepts presented herein:

Concept 1. An apparatus, comprising:
at least one conductive coil;
processing circuitry coupled to the at least one conductive coil and configured to (a) determine an inductance of the at least one conductive coil and (b) determine an identity of an object based on the inductance when an inductive identifier of the object is placed within a proximal distance of the at least one conductive coil.

Concept 2. The apparatus of concept 1 or any other concept, wherein the at least one conductive coil has a diameter and wherein the proximal distance of the at least one conductive coil comprises a distance from the conductive coil that is less than or equal to the diameter.

Concept 3. The apparatus of concept 1 or any other concept, wherein the inductive identifier comprises a patterned conductive film.

Concept 4. The apparatus of concept 1 or any other concept, wherein the inductive identifier comprises a patterned conductive ink.

Concept 5. The apparatus of concept 1 or any other concept, wherein the at least one conductive coil comprises a plurality of measurement coils and a reference coil.

Concept 6. The apparatus of concept 5 or any other concept, wherein inductive identifier comprises a plurality of features and wherein the processing circuitry is configured to determine the relative inductance of each of the measurement coils when a corresponding one of the plurality of features is within the proximal distance of that coil.

Concept 7. The apparatus of concept 6 or any other concept, wherein the processing circuitry is configured to identify the object based on the relative inductance of each of the measurement coils.

Concept 8. The apparatus of concept 7 or any other concept, wherein the processing circuitry is further configured to identify the object based on the inductance of the reference coil and a stored reference coil inductance.

Concept 9. A system comprising the apparatus of concept 1 or any other concept and the inductive identifier of the object.

Concept 10. The system of concept 9 or any other concept, wherein the apparatus comprises a cassette recess of an infusion pump system, wherein the object comprises a pump cassette coupled to an intravenous fluid set, and wherein the inductive identifier is disposed on the cassette.

Concept 11. A pump cassette, comprising:
a rigid body comprising a compliant membrane that defines a controllable fluid pathway that extends from an inlet port to an outlet port; and
an inductive identifier comprising a coded pattern that identifies the pump cassette.

Concept 12. The pump cassette of concept 11 or any other concept, wherein the inductive identifier comprises an inductive identifier film having a pattern of openings, the pattern of openings defining the coded pattern.

Concept 13. The pump cassette of concept 12 or any other concept, wherein the inductive identifier film comprises at least one conductive layer and wherein the pattern of openings comprise openings in the conductive layer.

Concept 14. The pump cassette of concept 13 or any other concept, wherein the inductive identifier film comprises a metalized biaxially-oriented polyethylene terephthalate film or a material heat fused with a polycarbonate (PC) copolymer or a methacrylate-acrylonitrile-butadiene-styrene (MABS) copolymer.

Concept 15. The pump cassette of concept 14 or any other concept, wherein the metalized biaxially-oriented polyethylene terephthalate film comprises aluminum.

Concept 16. The pump cassette of concept 11 or any other concept, wherein the coded pattern comprises a predetermined set of features each having a size, a shape, a density, or a composition configured to generate a corresponding inductance value in an inductive detector of an infusion pump system.

Concept 17. An infusion pump system, comprising:
a processing unit; and
a cassette recess adapted to receive a pump cassette, the cassette recess comprising:
an inductive cassette detector; and
a plurality of mechanisms operably coupled to the processing unit and configured to control fluid flow in pump cassette.

Concept 18. The infusion pump system of concept 17 or any other concept, wherein the inductive cassette detector comprises a plurality of conductive coils and readout circuitry configured to determine a pattern of inductance values corresponding to the pump cassette by using an inductance value of each of the conductive coils when a corresponding feature of an inductive identifier of the pump cassette is within a proximity of that conductive coil.

Concept 19. The infusion pump system of concept 18 or any other concept, further comprising the pump cassette, wherein the inductive cassette detector is configured to identify an IV set type based on the pattern of inductance values.

Concept 20. The infusion pump system of concept 17 or any other concept, wherein the plurality of mechanisms comprises a plurality of actuators configured to operate a piston and plurality of valves of the pump cassette.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

One or more aspects or features of the subject matter described herein may be realized in digital electronic circuitry, integrated circuitry, specially designed ASICs (application specific integrated circuits), computer hardware, firmware, software, and/or combinations thereof. For example, infusion pump systems disclosed herein may include an electronic system with one or more processors embedded therein or coupled thereto. Such an electronic system may include various types of computer readable media and interfaces for various other types of computer readable media. Electronic system may include a bus, processing unit(s), a system memory, a read-only memory (ROM), a permanent storage device, an input device interface, an output device interface, and a network interface, for example.

Bus may collectively represent all system, peripheral, and chipset buses that communicatively connect the numerous internal devices of electronic system of an infusion pump system. For instance, bus may communicatively connect processing unit(s) with ROM, system memory, and permanent storage device. From these various memory units, processing unit(s) may retrieve instructions to execute and data to process in order to execute various processes. The processing unit(s) can be a single processor or a multi-core processor in different implementations.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. An apparatus, comprising:
at least one conductive coil;
processing circuitry coupled to the at least one conductive coil; and
a pump cassette, the pump cassette comprising:
 a rigid body comprising:
  a compliant membrane that defines a controllable fluid pathway that extends from an inlet port to an outlet port,
  an interface-facing frame portion configured to face the at least one conductive coil in a cassette recess of an infusion pump, and
  a base portion, wherein the compliant membrane is disposed between the interface-facing frame portion and the base portion; and
 an inductive identifier comprising a coded pattern of at least two features that are laterally separated in a direction parallel to a surface of the interface-facing frame portion, the pattern of at least two features having an inductance that entirely identifies the pump cassette, wherein each of the at least two features is configured to be aligned with a corresponding conductive coil of the cassette recess when the rigid body is installed in the cassette recess,
wherein the processing circuitry is configured to (a) determine an inductance of the at least one conductive coil and (b) determine an identity of the pump cassette based on the inductance when the inductive identifier of the pump cassette is placed within a proximal distance of the at least one conductive coil.

2. The apparatus of claim 1, wherein the at least one conductive coil has a diameter and wherein the proximal distance of the at least one conductive coil comprises a distance from the conductive coil that is less than or equal to the diameter.

3. The apparatus of claim 1, wherein the inductive identifier comprises a patterned conductive film.

4. The apparatus of claim 1, wherein the inductive identifier comprises a patterned conductive ink.

5. The apparatus of claim 1, wherein the at least one conductive coil comprises a plurality of measurement coils and a reference coil.

6. The apparatus of claim 5, wherein the processing circuitry is configured to determine the relative inductance of each of the measurement coils when a corresponding one of the at least two features is within the proximal distance of that coil.

7. The apparatus of claim 6, wherein the processing circuitry is configured to identify the pump cassette based on the relative inductance of each of the measurement coils.

8. The apparatus of claim 7, wherein the processing circuitry is further configured to identify the pump cassette based on the inductance of the reference coil and a stored reference coil inductance.

9. The apparatus of claim 1, wherein the pump cassette is coupled to an intravenous fluid set.

10. A pump cassette, comprising:
a rigid body comprising:
 a compliant membrane that defines a controllable fluid pathway that extends from an inlet port to an outlet port,
 an interface-facing frame portion configured to face at least one conductive coil in a cassette recess of an infusion pump, and
 a base portion, wherein the compliant membrane is disposed between the interface-facing frame portion and the base portion; and
 an inductive identifier comprising a coded pattern of at least two features that are laterally separated in a direction parallel to a surface of the interface-facing frame portion, the pattern of at least two features having an inductance that entirely identifies the pump cassette, wherein each of the at least two features is configured to be aligned with a corresponding conductive coil of the cassette recess when the rigid body is installed in the cassette recess.

11. The pump cassette of claim 10, wherein:
the inductive identifier comprises an inductive identifier film on the surface of the interface-facing frame portion, the at least two features having a pattern of at least two openings that are laterally separated on the film in the direction parallel to the surface of the interface-facing frame portion, the pattern of at least two openings defining the inductance that entirely identifies the pump cassette.

12. The pump cassette of claim 11, wherein the inductive identifier film comprises at least one conductive layer and wherein the pattern of at least two openings comprises at least two discontinuous openings in the conductive layer.

13. The pump cassette of claim 12, wherein the inductive identifier film comprises a metalized biaxially-oriented polyethylene terephthalate film or a material heat fused with a polycarbonate (PC) copolymer or a methacrylate-acrylonitrile-butadiene-styrene (MABS) copolymer, and wherein the at least two openings have different sizes.

14. The pump cassette of claim 13, wherein the inductive identifier film comprises the metalized biaxially-oriented polyethylene terephthalate film, wherein the metalized biaxially-oriented polyethylene terephthalate film comprises a metallization layer on a biaxially-oriented polyethylene terephthalate film, the metallization layer comprising aluminum, and wherein the openings comprise openings in the metallization layer.

15. The pump cassette of claim 10, wherein the at least two features comprise a predetermined set of features each having a size, a shape, a density, or a composition configured to generate a corresponding inductance value in an inductive detector of an infusion pump system.

16. The pump cassette of claim 10, wherein the at least two features comprise a feature in a conductive material that is disposed between first and second insulating layers.

17. The pump cassette of claim 16, wherein the conductive material comprises aluminum.

18. The pump cassette of claim 10, wherein the inductive identifier comprises a patterned conductive ink.

19. The pump cassette of claim 10, wherein the inductive identifier comprises at least two conductive materials stacked on a substrate.

\* \* \* \* \*